United States Patent [19]
Hansenne et al.

[11] Patent Number: 6,096,294
[45] Date of Patent: Aug. 1, 2000

[54] PHOTOPROTECTIVE/COSMETIC COMPOSITIONS COMPRISING 2,4,6-TRIS[P-((2'-ETHYLHEXYL)OXYCARBONYL) ANILINO]-1,3,5-TRIAZINE AND SALICYLATE SOLVENTS THEREFOR

[75] Inventors: Isabelle Hansenne; Victoria Van Leeuwen, both of Paris, France

[73] Assignee: Societe L'Oréal S.A., Paris, France

[21] Appl. No.: 08/775,624

[22] Filed: Jan. 2, 1997

Related U.S. Application Data

[63] Continuation of application No. 08/463,508, Jun. 5, 1995, abandoned.

[30] Foreign Application Priority Data

Jun. 3, 1994 [FR] France ..................... 94 06831

[51] Int. Cl.$^7$ .................... A61K 7/42; A61K 7/40
[52] U.S. Cl. ............... 424/59; 424/60; 514/844; 514/938
[58] Field of Search .............. 424/59, 60; 514/844, 514/938

[56] References Cited

U.S. PATENT DOCUMENTS 5,302,376   4/1994   Forestier et al. ................ 424/59

FOREIGN PATENT DOCUMENTS

| 457 587 | 5/1991 | European Pat. Off. |
| 0457687 | 11/1991 | European Pat. Off. |
| 0521651 | 1/1993 | European Pat. Off. |
| 2278055 | 11/1994 | United Kingdom |

OTHER PUBLICATIONS

Shaath, N., "Encyclopedia of UV Absorbers for Sunscreen Products" Cosmetic Toiletries, vol. 102, Mar. 1987 pp. 21–36.

Roelandts, R et al. "A Survey of Ultraviolet Absorbers in Commercially Available Sun Products" International Journal of Dermatology, May 1983, vol. 22, pp. 247–255.

Positivlisti Zur Kosmetikverordnung "Raw Materials in Cosmetics and Toiletries," Roland Langner Seifer–Ol$_2$–Feitz–Wachse, No. 7, 1980, p. 200.

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise (i) a photoprotecting effective amount of 2,4,6-tris[p-((2'-ethylhexyl) oxycarbonyl)anilino]-1,3,5-triazine and (ii) at least one homomenthyl and/or octyl salicylate solvent for the triazine sunscreen compound (i), in a cosmetically acceptable vehicle, diluent or carrier therefor.

21 Claims, No Drawings

PHOTOPROTECTIVE/COSMETIC COMPOSITIONS COMPRISING 2,4,6-TRIS[P-((2'-ETHYLHEXYL)OXYCARBONYL)ANILINO]-1,3,5-TRIAZINE AND SALICYLATE SOLVENTS THEREFOR

This application is a continuation of application Ser. No. 08/463,508, filed Jun. 5, 1995, now abandoned.

CROSS-REFERENCE TO COMPANION APPLICATIONS

Copending applications Ser. No. [Attorney Docket No. 016800-028], Ser. No. 08/463,221 [Attorney Docket No. 016800-029], Ser. No. 08/463,505 [Attorney Docket No. 016800-030], Ser. No. 08/463,503 U.S. Pat. No. 5,489,431 [Attorney Docket No. 016800-031], Ser. No. 08/463,762 [Attorney Docket No. 016800-032], Ser. No. 08/463,304 [Attorney Docket No. 016800-034], Ser. No. 08/461,015 [Attorney Docket No. 016800-035], Ser. No. 08/463,507 [Attorney Docket No. 016800-036], Ser. No. 08/464,940 each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, typically an oil-in-water emulsion, combinatory immixture of (i) the lipophilic organic sunscreen compound 2,4,6-tris[p-((2'-ethylhexyl)oxycarbonyl)anilino]-1,3,5-triazine and (ii) at least one other judiciously selected specific lipophilic sunscreen compound that solubilizes said triazine compound (i) therein.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

One organic sunscreen compound having desirable properties and which to date has been widely used is 2,4,6-tris [p-((2'-ethylhexyl)oxycarbonyl)anilino]-1,3,5-triazine, a lipophilic sunscreen compound which is highly active in the UV-B range, photostable and water-resistant. This compound is marketed under the trademark "UVINUL T 150" by BASF. Nonetheless, it presents the disadvantage of being solid at room temperature. For this reason, incorporating same into sunscreen/cosmetic compositions entails certain constraints as regards its formulation and application, in particular in the selection of the solvents permitting proper dissolution thereof. In this respect, solvent oils are typically employed, such as triglycerides and in particular triglycerides of $C_8$–$C_{12}$ fatty acids ("Miglyol 812" marketed by Hüls), or, alternatively, of oxyethylenated or oxypropylenated fatty mono- or polyalcohols ("Cetiol HE" marketed by Henkel or "Witconol APM" marketed by Witco), or mixtures thereof. These oils nevertheless present certain disadvantages, in particular that, on the one hand, they exhibit no specific (or intrinsic) activity in respect of screening UV radiation (UV-A and UV-B) and, on the other, that their solubilizing properties with respect to the aforesaid triazine sunscreen compound still remain unsatisfactory, both as regards the solubility limits thereof and the rates of solubilization of this triazine compound in these solvents.

SUMMARY OF THE INVENTION

It has now unexpectedly and surprisingly been determined that homomenthyl salicylate (also known more simply as "homosalate") and octyl salicylate, as well as mixtures thereof, are conspicuously very good solvents for 2,4,6-tris [p-((2'-ethylhexyl)oxycarbonyl)anilino]-1,3,5-triazine. Indeed, this triazine sunscreen compound exhibits relatively high solubilities in the aforesaid salicylate compounds, which solubilities are, in all instances, markedly better than those obtained using the other conventional solvents to date characterizing the state of this art. It is thus possible, with an equal amount of solvent, to formulate greater amounts of the triazine sunscreen compound.

Too, the rate at which 2,4,6-tris[p-((2'-ethylhexyl) oxycarbonyl)anilino]-1,3,5-triazine dissolves in the two salicylate solvents indicated above is remarkably improved, which presents a considerable advantage on an industrial production scale (savings in time and in energy in the mixing operations, and therefore in overall output, and lower production costs). It will also be appreciated that homomenthyl salicylate, on the one hand, and octyl salicylate, on the other, are liquid lipophilic screening compounds already known to be active in the UV-B range, but their solubilizing properties in respect of the above solid triazine sunscreen compound have never been described.

Thus, the advantages of the present invention are manifold in that not only can the 2,4,6-tris[p-((2'-ethylhexyl)

oxycarbonyl)anilino]-1,3,5-triazine be solubilized in a novel solvent, itself per se advantageous, but also such solubilization is improved (increased solubility and increased rate of solubilization), while at the same time providing a substantial increase, at an equal concentration of the triazine sunscreen compound in the final sunscreen/cosmetic composition, in the level of photoprotection imparted thereby.

Briefly, the present invention features novel photoprotective/cosmetic compositions comprising, in a cosmetically acceptable vehicle, diluent or carrier, (i) an effective sunscreen amount of 2,4,6-tris[p-((2'-ethylhexyl)oxycarbonyl)anilino]-1,3,5-triazine, and (ii) an effective solubilizing amount of at least one of the solvents, homomenthyl salicylate, octyl salicylate, or mixture thereof.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

This invention, thus, also features the use of homomenthyl salicylate and/or octyl salicylate as solvent(s) in sunscreen/cosmetic compositions comprised of 2,4,6-tris[p-((2'-ethylhexyl)oxycarbonyl)anilino]-1,3,5-triazine.

DETAILED DESCRIPTION OF BEST MODE AND PREFERRED EMBODIMENTS OF THE INVENTION

More particularly according to the present invention, 2,4,6-tris[p-((2'-ethylhexyl)oxycarbonyl)anilino]-1,3,5-triazine (compound A) is a sunscreen compound that is per se known to this art and is active in the UV-B range, is a solid material and is marketed under the trademark "UVINUL T 150" by BASF. This compound has the following structural formula (I):

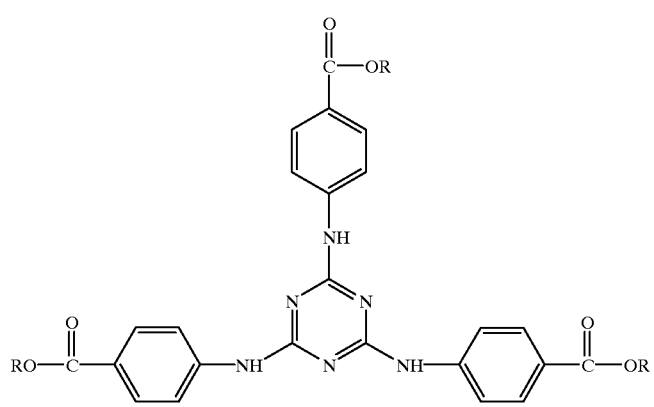

in which R is a 2-ethylhexyl radical.

The triazine sunscreen compound (i) is advantageously present in the compositions according to the invention at a concentration ranging from 0.5% to 15% by weight relative to the total weight of the composition. In a particularly preferred embodiment of this invention, said triazine compound (i) must exist in the final sunscreen/cosmetic compositions in an entirely, or substantially entirely, dissolved state.

The homomenthyl salicylate (compound B, a solvent for the compound A), also known as "homosalate," is also commercially available and is marketed, in particular, under the trademark "Kemester HMS" by Witco. It has the following structural formula (II):

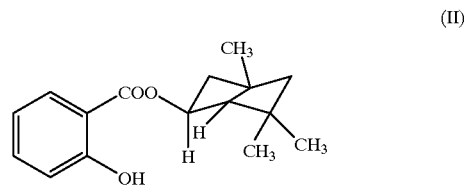

The octyl salicylate (compound C, also a solvent, whether or not jointly with the other solubilizing compound B, for the compound A) is marketed, in particular, under the trademark "UVINUL O-18" by BASF. It has the following structural formula (III):

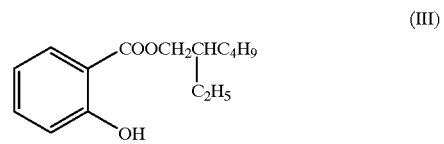

The compounds B and/or C (solubilizers) are advantageously present in the sunscreen/cosmetic compositions according to the invention at a concentration ranging from 0.5% to 25% by weight relative to the total weight of the composition. In a particularly preferred and advantageous embodiment of the invention, these compounds B and/or C are employed in amounts sufficient to themselves dissolve the total amount, or substantially the total amount, of the compound A present in the composition. This minimum amount of solvent(s) for the complete and stable dissolution of the solid triazine sunscreen compound (i) can readily be determined from the solubility parameters of said screening compound in these solvents.

For example, at room temperature, the compound A is soluble in a proportion of approximately 16% by weight in the solvent compound B and in a proportion of approximately 25% by weight in the solvent compound C.

Moreover, the concentrations and ratios of the sunscreen compound (i) and the salicylates (ii) are typically selected such that the sun protection factor of the final composition is preferably at least 2.

In another particularly preferred embodiment of the invention, the final sunscreen/cosmetic compositions preferably contain no solubilizer or substantially no solubilizer for the compound A, other than the compound(s) B and/or C described above. According to the invention, a given compound is considered as not possessing solubilizing properties with respect to another given compound when the latter compound has a solubility of less than approximately 1% by weight in the first compound.

In a preferred embodiment of the present invention, the cosmetically acceptable vehicle, diluent, carrier or support in which the compounds A, B and/or C are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, $\beta,\beta$-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, $\alpha$-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-$\alpha$-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, J. Mol. Biol, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation. If desired, the fatty phase of the emulsions according to the invention may comprise only or essentially only the salicylates B and/or C (organic solvents) in which the triazine compound A is dissolved, together with the optional additional screening agents and other conventional lipophilic cosmetic additives and adjuvants.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

In this example, the time required for solubilization of 2,4,6-tris[p-((2'-ethylhexyl)oxycarbonyl)anilino]-1,3,5-triazine ("Uvinul T 150" marketed by BASF) in various solvents was determined by means of the following test:

(i) 10 g of solvent were added to 5 g of the photoprotective/sunscreen agent Uvinul T 150 at room temperature.

(ii) the mixture thus obtained was heated to 83° C. using a water bath, and (iii) the time (in minutes) which was required to completely dissolve the photoprotective/sunscreen agent after this temperature had been attained was then recorded.

The results obtained are reported in the Table below (the chemical names are given in the CTFA nomenclature, 5th edition, 1993):

TABLE

| SOLVENT | SOLUBILIZATION TIME (min) | |
|---|---|---|
| Octyl salicylate ("Uvinul 0–18" marketed by BASF) | 0 | Invention |
| Homosalate ("Kemester HMS" marketed by Witco) | 3 | |
| Triglycerides of $C_8$–$C_{12}$ fatty acids ("Miglyol 812" marketed by Hüls) | 10 | Comparative |
| PEG-7 Glyceryl Cocoate ("Cetiol HE" marketed by Henkel) | 10 | |
| PPG-3 Myristyl Ether ("Witconol APM" marketed by Witco) | 15 | |

These results clearly demonstrate the superior solubilizing power of the two solvents in accordance with the invention.

EXAMPLE 2

A specific formulation of a composition according to the invention, in the form of an emulsion of oil-in-water type, is as follows:

| (a) | 2,4,6-Tris[p-((2'-ethylhexyl)-oxycarbonyl)anilino]-1,3,5-triazine ("Uvinul T 150 marketed by BASF) | 3 g |
|---|---|---|
| (b) | Homosalate | 5 g |
| (c) | Octyl salicylate | 10 g |
| (d) | Polydimethylsiloxane | 1.5 g |

-continued

| (e) | Cetyl alaohol | 1.5 g |
|---|---|---|
| (f) | Liquid paraffin | 5 g |
| (g) | Glyceryl mono/distearate mixture | 2 g |
| (h) | Mixture of cetylstearyl alcohol and of cetylstearyl alcohol oxyethylenated with 33 mol of ethylene oxide (80%/20%) ("Cire de Lanol CTO" marketed by Seppic) | 7 g |
| (i) | Glycerol | 4 g |
| (j) | Titanium dioxide, nanopigment grade | 2 g |
| (k) | Preservatives | qs |
| (l) | Water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising (i) a photoprotecting effective amount of 2,4,6-tris[p-((2'-ethylhexyl)oxycarbonyl)anilino]-1,3,5-triazine and (ii) at least one homomenthyl and/or octyl salicylate solvent for said triazine sunscreen compound (i), in a cosmetically acceptable vehicle, diluent or carrier therefor.

2. The sunscreen/cosmetic composition as defined by claim 1, the amount of said at least one homomenthyl and/or octyl salicylate solvent (ii) being sufficient to essentially completely dissolve the total amount of said triazine sunscreen compound (i).

3. The sunscreen/cosmetic composition as defined by claim 1, substantially devoid of any solvent for said triazine sunscreen compound (i), other than said at least one homomenthyl and/or octyl salicylate solvent (ii).

4. The sunscreen/cosmetic composition as defined by claim 1, comprising from 0.5% to 15% by weight of said triazine compound (i).

5. The sunscreen/cosmetic composition as defined by claim 4, comprising from 0.5% to 25% by weight of said at least one homomenthyl and/or octyl salicylate solvent (ii).

6. The sunscreen/cosmetic composition as defined by claim 1, comprising an oil-in-water emulsion.

7. The sunscreen/cosmetic composition as defined by claim 1, comprising a water-in-oil emulsion.

8. The sunscreen/cosmetic composition as defined by claim 1, further comprising at least one additional hydrophilic or lipophilic organic UV-A and/or UV-B sunscreen.

9. The sunscreen/cosmetic composition as defined by claim 8, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

10. The sunscreen/cosmetic composition as defined by claim 1, further comprising a photoprotecting effective amount of particulates of at least one inorganic pigment or nanopigment.

11. The sunscreen/cosmetic composition as defined by claim 10, said at least one pigment or nanopigment comprising titanium dioxide, zinc oxide, iron oxide, zirconium oxide, cerium oxide, or mixture thereof.

12. The sunscreen/cosmetic composition as defined by claim 1, further comprising at least one active agent for the artificial tanning and/or browning of human skin.

13. The sunscreen/cosmetic composition as defined by claim 1, further comprising at least one cosmetically acceptable adjuvant or additive.

14. The sunscreen/cosmetic composition as defined by claim 13, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

15. The sunscreen/cosmetic composition as defined by claim 1, comprising a nonionic vesicle dispersion, emulsion, cream, milk, gel, cream gel, ointment, suspension, dispersion, powder, solid stick, foam or spray.

16. The sunscreen/cosmetic composition as defined by claim 1, comprising a makeup.

17. The sunscreen/cosmetic composition as defined by claim 16, comprising an anhydrous or aqueous solid or paste, emulsion, suspension, or dispersion.

18. The sunscreen/cosmetic composition as defined by claim 1, comprising a shampoo, lotion, gel, emulsion, nonionic vesicle dispersion, hair lacquer, or rinse.

19. The sunscreen/cosmetic composition as defined by claim 1, having a sun protection factor of at least 2.

20. A method for protecting human skin and/or hair against the deleterious effects of ultraviolet irradiation, comprising topically applying thereto an effective amount of the sunscreen/cosmetic composition as defined by claim 1.

21. A method for protecting human skin and/or hair against the deleterious effects of solar radiation, comprising topically applying thereto an effective amount of the sunscreen/cosmetic composition as defined by claim 1.

* * * * *